United States Patent [19]

Duncan et al.

[11] Patent Number: 5,964,987
[45] Date of Patent: Oct. 12, 1999

[54] NEUTRAL OIL REMOVAL FROM NATURAL CRESYLIC ACID MIXTURES

[75] Inventors: David H. Duncan, Dodge; Gene G. Baker, Hazen; Dana J. Maas, Hazen; Kevin M. Mohl, Hazen; Alfred K. Kuhn, Beulah, all of N. Dak.

[73] Assignee: Dakota Gasification Company, Beulah, N. Dak.

[21] Appl. No.: 08/929,550

[22] Filed: Sep. 15, 1997

[51] Int. Cl.⁶ .............................. B01D 3/34; C07C 37/72; C07C 37/74

[52] U.S. Cl. ................................. 203/51; 203/52; 203/68; 203/69; 203/70; 203/71; 203/91; 203/94; 203/99; 203/DIG. 19; 568/751; 568/761

[58] Field of Search .................................. 203/51, 52, 43, 203/99, DIG. 19, 68, 70, 69, 94, 91, 71, 44–46; 568/749, 750, 751, 752, 753, 761

[56] References Cited

U.S. PATENT DOCUMENTS

| | | | |
|---|---|---|---|
| 2,666,796 | 1/1954 | Gorin et al. | 568/761 |
| 2,766,296 | 10/1956 | Jones et al. | 568/761 |
| 2,790,834 | 4/1957 | Morton et al. | 568/749 |
| 2,806,886 | 9/1957 | Neuworth | 568/761 |
| 2,888,491 | 5/1959 | Herbert et al. | 568/761 |
| 3,153,626 | 10/1964 | Kulik | 208/22 |
| 3,277,185 | 10/1966 | Eisenlohr et al. | 568/761 |
| 5,171,895 | 12/1992 | Brient | 568/761 |
| 5,354,429 | 10/1994 | Duncan et al. | 203/59 |
| 5,679,223 | 10/1997 | Duncan et al. | 203/64 |
| 5,750,009 | 5/1998 | Duncan et al. | 203/78 |

FOREIGN PATENT DOCUMENTS 730473  5/1955  United Kingdom.

OTHER PUBLICATIONS

Cumming, A.P.C., and Morton, F., "Solvent Extraction of Phenol from Coal–Tar Hydrocarbons: The Use of Glycerol, Triethylene Glycol and Their Aqueous Solutions as Solvents", J. appl. Chem., Jun. 2, 1952, pp. 314–323.

Cumming, A.P.C., "Separation of Phenols from Coal–Tar Hydrocarbons by Means of Glycerol and Aqueous Trithylene Glycol: Development of a Process", J. appl. Chem., Mar. 3, 1953, pp. 98–106.

Primary Examiner—Virginia Manoharan
Attorney, Agent, or Firm—Alix, Yale & Ristas, LLP

[57] ABSTRACT

Natural cresylic acid is processed to remove neutral oil impurities by countercurrent liquid/liquid extraction using a heavy phase solvent of a mixture of glycerol and another polyhydric alcohol, preferably triethylene glycol. The light phase solvent is a light paraffinic or cycloparaffinic hydrocarbon.

5 Claims, 1 Drawing Sheet

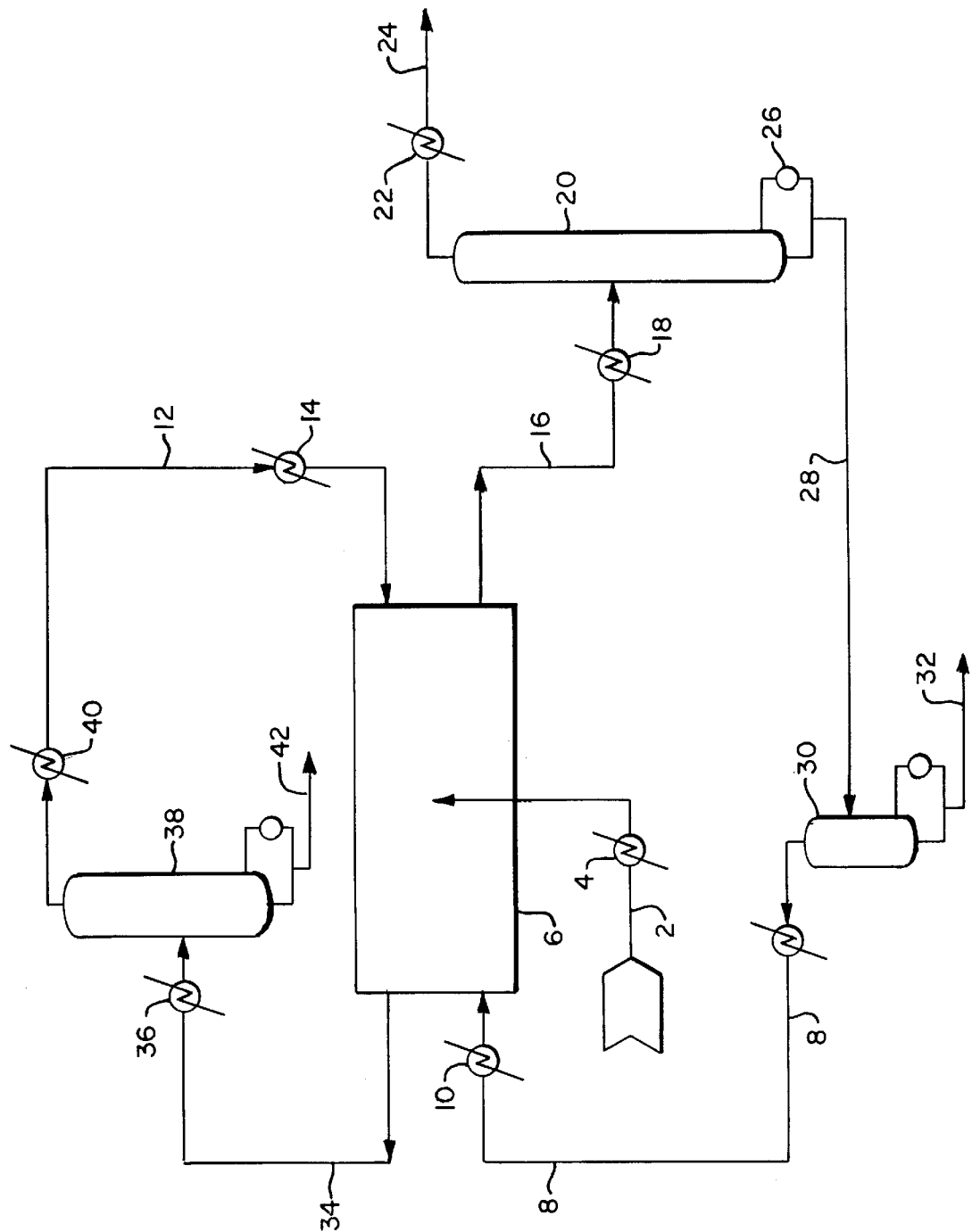

NEUTRAL OIL REMOVAL FROM NATURAL CRESYLIC ACID MIXTURES

FIELD OF THE INVENTION

The field of this invention is liquid/liquid fractional countercurrent extraction, as applied to the separation of neutral oil impurities from natural cresylic acid mixtures.

BACKGROUND OF THE INVENTION

Feedstocks containing natural cresylic acid, a mixture of phenol, cresols, ethylphenols, xylenols and $C_9$ phenols, are obtained via petroleum processing or coal processing. All such feedstocks contain neutral oil and tar bases. Neutral oil as used throughout this text is a class of organic compounds which is regarded as being comprised of impurities, and is indigenous to natural cresylic acid feedstocks. Any individual substance in neutral oil is a compound which is neither acidic, as are phenols, nor basic, such as the tar bases (pyridine and its homologues often in mixture with aniline and its homologues), but is by nature neutral in its reactions.

Spent caustic from petroleum refining is obtained by way of extraction of refinery distillates with sodium hydroxide. It contains significant amounts of cresylic acid and neutral oil impurities. According to the prior art, this spent caustic is processed by first removing sulfur compounds and then neutral oil compounds and tar bases are removed via steam distilling from the caustic solution. The cresylic acid is then "sprung" by reaction of the caustic cresylate with an acid. Finally, the sprung phenolic oil is dried by distillation to remove the water and then it is distilled to separate the cresylic acid from pitch which is a high boiling residue material. Such a process provides a raw cresylic acid mixture suitable for the present invention provided the steaming step for removal of neutral oil and tar bases is either eliminated or reduced in severity. Such a feedstock would also be suitable if dephenolized by distillation to remove phenol.

Coal processing technologies, such as coking, gasification or other coal devolatilization or beneficiation processes all yield at least two condensate streams, coal tar oil, and phenolic-rich condensate water.

These result from cooling of gaseous devolatilization products from coal. Coal tar oil may be used as a feedstock from which to obtain a distillate fraction containing cresylic acid. Coal tar oil may be distilled to separate water and light ends (the latter is often an aromatic naphtha), and also a carbolic oil distillate, also known as tar oil distillate, which contains cresylic acid. This material contains large amounts of neutral oil, often in the range of 50% to 70%, and relatively small amounts of tar bases (frequently in the 3% to 6% range). This feedstock may be processed to remove the impurities by any of a number of prior art techniques. This feedstock is a candidate material for the present invention, or this material could be dephenolized and then used as a feedstock. Once purified, including final tar base removal, the cresylic acid may be sold as such, or distilled into various products, such as cresols, or xylenols, or mixtures of these with other phenols.

Phenolic-rich condensate water (gas liquor) is most often extracted with a solvent such as an ether, ester, ketone, or a light aromatic to extract the phenols contained therein. After removal of the solvent, this mixture of phenols is often called crude phenol. Such crude phenol may be distilled to separate the cresylic acid fraction, which is the monohydric phenol fraction, from pitch. The pitch often contains dihydric phenols. The cresylic acid fraction can then be dried by distillation to remove the water and light ends which distill along with the water. The dried and depitched material (raw cresylic acid) thus obtained is far less neutral oil-rich than the tar oil distillate described above. This raw cresylic acid typically contains about 1.5% to 5% neutral oil, and 1.5% to 4% tar bases. This material can also be processed by any of a number of prior art techniques, to achieve purification, to prepare it for either sale, or fractionation and then sale. It is also a candidate material for the present invention either as such, or dephenolized.

The tar oil distillate feedstocks have in the past been purified by way of any of three types of process technologies. These categories are (1) causticizing, usually with sodium hydroxide, and steam distilling the neutral oil and tar bases, followed by springing the wet phenolic oil, (2) any of various single solvent approaches to the task of extraction of cresylic acid from neutral oil, and (3) any of numerous dual solvent technologies, using a two phase immiscible pair of solvents, one to dissolve the phenols, and another to dissolve the neutral oil, followed by solvent recovery systems for separation of the solvents from the product phenols, and from the neutral oil. Additionally, the Phenoraffin process is suitably classified as a dual solvent system, but it is a hybrid in the sense that it employs sodium ion in the form of sodium cresylate as one of the solvents, and in the sense that some of the neutral oil is removed in a distillation step to recover toluene.

The first of the above three categories is the oldest of the cresylic acid processing methods. After causticizing the feedstock (not needed in the case of spent caustic which is already causticized), the caustic phase is decanted away from any insoluble neutral oil. In the case of spent caustic, there is no floating neutral oil since the spent caustic is decanted at the refinery and, in the case of crude phenol extract from gas liquor or the like, there is not enough neutral oil present to form a neutral oil phase. The next step consists of steam distilling the neutrals and tar bases dissolved in the caustic cresylate. Following this, an acid is used to spring the wet phenolic oil. The wet sprung cresylic acid is next dried by distilling away the water. When required, the cresylic acid may be distilled to separate it from materials which are pitch-like, or a small amount of sulfuric acid may be added and this mixture distilled, to separate the cresylic acid from traces of tar bases not thoroughly steamed out, as well as from pitch-like materials.

This prior technology, particularly if sodium hydroxide must be purchased or regenerated, is costly, and also quite bulky and energy intensive. If caustic is not regenerated from process byproduct sodium carbonate (obtained via carbon dioxide springing of the wet phenolic oil) by way of quicklime, then the sodium-containing waste stream must be transported and sold.

The single solvent extraction methods employ a polar solvent to extract the phenols from tar oil distillates of various kinds. These methods employed aqueous solutions of a number of solvents, such as glycols, ethanolamine, ammonia, acetic acid, ethylamine, sodium salicylate, methanol, or even hot water. Distillation was typically used to separate the solvent from the extract for recycle. All of these methods provided cresylic acid containing too much neutral oil to be salable in today's market.

Because of the purity vs. yield problem with the single solvent approaches, dual solvent systems were developed, utilizing fractional, side feed, countercurrent extraction as opposed to ordinary countercurrent extraction. These processes utilized a polar solvent to dissolve the cresylic acid and a non-polar solvent to dissolve the neutral oil. The side feed fractional aspect of these methods permitted a number of liquid/liquid equilibrium stages to be used in the process to separate one component of a feedstock from another. This granted the ability to exercise control over both purity (the number of stages employed in the direction of removal of the heavy solvent), and recovery (yield of cresylic acid by way of the number of stages in the direction of removal of the light solvent). Included among the polar solvents used have been aqueous solutions of methanol, ammonia, acetamide, acetic acid, ethanol, glycols, monoethylamine and sodium salts of sulfonic acids. Non-aqueous polar solvents have included glycols of various kinds, and glycerol. Light, non-polar solvents have included hexane, heptane, octane, petroleum ether, diesel, and various non-aromatic naphthas. Distillation was generally used to separate the solvents from the extract and the raffinate to ready them for recycle and to isolate the phenolic product and neutral oil streams.

The best known of the dual solvent fractional extraction methods is that disclosed in U.S. Pat. No. 2,666,796 which uses aqueous methanol and hexane. The literature available from the 1950's regarding this process shows that neutral oil contents of about 0.2% or even 0.1%, are possible. It must be said, though, that the analytical methods used at that time are far from adequate to reveal all of the neutral oil actually present in a cresylic acid material.

The earlier methods of neutral oil analysis were based on causticizing a sample of cresylic acid and steam distilling the neutral oil and tar bases from the sample. Following this, the tar bases were titrated, and finally the volume of neutral oil present in the distillate was measured and multiplied by a specific gravity factor to arrive at a weight percent neutral oil. This method is now out-dated. It is not capable of revealing very much of the ketone content (especially the cyclopentenone homologues), or the content of nitriles (much of the ketone content is destroyed by the action of boiling caustic, as well as most of the benzonitrile), nor will it reveal the most polar among the neutral oil substances that are inclined to dissolve in the steam distillate water phase. The modern technique employs a number of methods, each designed to reveal a particular class of neutral oil substances or an individual substance, to arrive at an accurate total neutral content for a sample.

The cresylic acid product of the subject invention, derived from tar oil distillate, does not reveal any neutral oil at all by the old method of measuring the volume of oil in a steam distillate even though the water phase can exhibit a slight haziness. Thus, by the older methods, this product would be said to have nil, or zero neutral oil content, not enough to form a detectable amount of oil to measure an oil volume. Using a tar oil distillate as a feedstock to the subject invention, it has been found that the neutral oil contents of products of various dual solvent methods of prior art, as determined by modern methods of analysis, are roughly an order of magnitude greater than the results reported from steam distillation of a causticized sample using the old measuring techniques. It is very difficult to even force the prior art process to the point where cresylic acid products have less than 1% neutral oil content as analyzed using modern analytical methods.

One of the problems of prior art methods which employed aqueous, light boiling solvents is that after removal by distillation of the solvent such as methanol, the bottoms product is two phases, wet cresylic acid product and water. Decanting the water from the wet cresylic acid is troublesome at best. The water phase coalesces and separates from wet cresylic acid with difficulty. Once the water is coalesced, and the wet cresylic acid is decanted away from it, the residual dissolved water must be distilled from the cresylic acid and this is quite energy intensive. Thus, there has been an incentive to use dry solvents to avoid these problems.

Several investigations have been done, using triethylene glycol as the extractant, and alternately, using glycerol as the extractant. A paper describing such studies appears in the *Journal of Applied Chemistry*, June, 1952, p.314. Ternary solubility diagrams were provided for the systems phenol, triethylene glycol and hydrocarbon (a coal tar hydrocarbon distillate fraction), and also for phenol, glycerol and hydrocarbon, at three temperatures. Additionally, the effect of several amounts of added water to the systems was defined in solubility diagrams. Results showed that the effect of water added to the triethylene glycol system was favorable, indicating that limited addition of water to triethylene glycol provided an improved product, containing less neutral oil. The effect of water upon glycerol was unfavorable, though, as the glycerol phase in the presence of added water tended to dissolve more of the neutral oil hydrocarbon than if the glycerol were anhydrous.

Another paper, published in March of 1953, also in the *Journal of Applied Chemistry* reports a similar study excepting that the system studied was cresylic acid, triethylene glycol or glycerol, and a hydrocarbon distillate derived from coal. The solubility of the mixed phenols in the glycerol was quite low, so much so that a large number of stages would be required to achieve good recovery from the raffinate. Also, the neutral oil solubility in the glycerol phase was greater. Thus, the separation was not as desirable as in the above mentioned system using phenol, rather than mixed phenols. In other words, the phenolics were not adequately soluble in the glycerol and the neutral oils were more soluble than in the earlier study. It was concluded that glycerol was not recommended for the extraction of mixed phenols. For triethylene glycol, the solubility of the phenolics was good using triethylene glycol containing 37% water. It was reported that it would be possible to obtain a product containing 0.1% neutral oil, but the actual content would probably be determined to be much higher using modern analytical methods.

In the development of the present invention, studies of anhydrous triethylene glycol have shown that even using modern high efficiency fractional countercurrent extraction equipment such as the Karr column having approximately seven to eight equilibrium stages, it was not possible to achieve a total neutral oil content in cresylic acid products less than the 1% to 2% range, as analyzed using modern analytical techniques. The studies with tar oil distillate feedstock have shown that the well known wet methanol/ hexane system, using modern extraction equipment and analytical methods, also provides cresylic acid containing neutral oil in the 1% to 2% range, at best.

If one were to use aqueous triethylene glycol, it would be mandatory to distill all of the water to separate it from the product cresylic acid since, unlike wet methanol, the glycol has a boiling point greater than that of the cresylic acid. After methanol has been removed by distillation, it is possible to decant water from cresylic acid since a sizable fraction of the water then forms a separate phase. No comparable process option exists with triethylene glycol. Distillation of water is very energy intensive and therefore quite uneconomic on a commercial basis.

The work mentioned above appearing in the *Journal of Applied Chemistry* eventuated in U.S. Pat. No. 2,790,834 and British Patent 730,473. As in the published papers, the preferred heavy extraction solvent employed was either an aqueous solution of triethylene glycol, or alternately glycerol which was said to be less desirable for extraction of mixed phenols for reason of high solvent ratio and increased number of extraction stages required to extract the phenolics. Other polyhydric alcohol solvents were also discussed.

The literature of Cumming and Morton indicated that they found glycerol to be inadequately capable of extracting mixed phenols (cresylic acid) and this is supported by tests leading up to the present invention. In terms of polarity and degree to which hydrogen bonding occurs, only water exceeds glycerol, in data tables listing solvents which are industrially available.

Bench scale studies with glycerol revealed that this solvent is very nearly incapable of extracting cresylic acid from tar oil distillate; so little of the cresylic acid would partition into glycerol that the glycerol remained very nearly colorless. As noted above, triethylene glycol, in an anhydrous state, performed quite well in terms of its ability to extract the cresylic acid from an aromatic neutral oil matrix, so well, in fact, that it was insufficiently capable of rejecting the most difficult of the various neutral oil substances such as the ketones, the naphthalenes and the nitrites. Triethylene glycol can be used in an anhydrous state, and this is a very desirable aspect of its use, but the purity of the products achieved with it is at least an order or magnitude, if not twice an order, worse than desired.

Upon first investigating triethylene glycol (dry) with a Karr column, using tar oil distillate, it was discovered that nitrites, similar to the performance of the wet methanol, were poorly removed, and the content of naphthalene and its homologues was found to be significantly worse than when using aqueous methanol. The ketones were a little more readily removed. The tar oil distillate used for all of these studies contained about 60% neutral oil.

The studies of the aqueous methanol/hexane approach to neutral oil removal, using a Karr column, or alternatively a mixer settler arrangement, revealed that this solvent system is fairly effective at separating naphthalene and its homologues from cresylic acid (products from tar oil distillate can be obtained at less than 100 ppm naphthalenes), but quite poor in separation of ketones (products range from 1% to 3.5%) and nitriles (products at best contain about 1000 ppm total nitrites).

To simultaneously obtain high product recovery and high product purity has not been possible via any of the liquid/liquid countercurrent fractional extraction techniques of prior art that have been studied using identical feedstocks.

SUMMARY OF THE INVENTION

It has been discovered that mixtures of glycerol and triethylene glycol are greatly superior to any other heavy phase solvent disclosed in the field of natural cresylic acid processing with regard to the ability of this solvent to achieve separation of neutral oil species from cresylic acid. In the method of the present invention, the heavy phase used as the solvent for dissolving the cresylic acid is a mixture of glycerol and another polyhydric alcohol, preferably triethylene glycol, and the light phase used as the solvent for dissolving the neutral oil impurities is a light paraffinic or cycloparaffinic hydrocarbon such as hexane, heptane or cyclohexane or various mixtures of paraffins and/or cycloparaffins, which also could be mixed with light aromatic solvents. This heavy solvent mixture in tandem with the light, non-polar solvent is capable of affording both high recovery of cresylic acid from feedstocks containing cresylic acid, in the range of 92% to 97%, and also product purities ranging from 200 ppm to 800 ppm total neutral oil.

BRIEF DESCRIPTION OF THE DRAWING

The drawing is a block flow diagram of the preferred embodiment of the process of the present invention.

DESCRIPTION OF THE PREFERRED EMBODIMENTS

In the development of the present invention, it was conceived that if glycerol is too polar to extract cresylic acid from an aromatic neutral oil matrix, then it might be used to enhance the polarity of another solvent (provided the boiling point spread between glycerol and the other solvent would not result in an impractical system). Upon realizing that glycerol could be used to improve the polarity of a glycol (ideally triethylene glycol, given that it has a boiling point not too distant from glycerol), the distribution coefficients in this mixed heavy phase solvent system were measured using hexane as the light solvent. Coefficients were measured of numerous neutral oil species, including highly polar substances such as the ketones and benzonitrile, all of which are found in the lignite-derived tar oil distillate tested. The coefficients of the phenolics present in tar oil distillate were also measured. It was found that a solvent system which is fairly rich (65% to 85%) in glycerol, and less in triethylene glycol (35% to 15%), provided coefficients more favorable for neutral oil removal than seen for any other dry solvent system studied. For nearly all neutral oil species, this mixed solvent performs better than the various aqueous systems which rely upon water to provide high solvent polarity. The coefficients measured for the phenolics (which indicate the extent to which the phenols can be recovered from a feedstock) were much better than for pure glycerol. It was then concluded that good recovery of cresylic acid could be obtained simultaneously with high purity.

Pilot plant trials confirmed the expectations, and it was found possible to produce from tar oil distillate a cresylic acid product that exhibited, in the traditional neutral oil test (steam distillation of a causticized sample), only a slight haziness in the test's condensate water, and no observable oil to measure. More sophisticated analytic testing has shown that this cresylic acid product, after treatment with sulfuric acid to remove tar bases and achieve a further reduction in cyclopentenones, contains less than 800 ppm of total neutral oil species, including less than 200 ppm of total benzonitriles, 210 ppm cyclopentenones, less than 25 ppm total naphthalenes, and the balance of other neutral species. Such product was obtained, using a heavy solvent mixture containing 65% glycerol, at recoveries of about 92% (of the total cresylic acid in the tar oil distillate, biased in favor of recovery of the lighter phenols, and against recovery of the $C_9$ phenols).

In pilot plant testing, using dried and depitched cresylic acid fraction from extract from gas liquor, it was possible to obtain products containing about 200 ppm total neutral oil, comprised of less than 170 ppm total benzonitriles, less than 5 ppm total naphthalenes, and the balance other neutral species (cyclopentenones were not detectable, with a method having a lower limit of 150 ppm for the total of these substances). This product was obtained at 96.8% recovery.

The performance of this system with a tar oil distillate feedstock is at least one order of magnitude better in product purity than any other method of prior art investigated. Other researchers have studied these solvents individually, but no one in the cresylic acid industry has proposed that glycerol and glycol could be used in a mixed solvent heavy phase system. This discovery is of great value to the cresylic acid industry, given the product quality obtained from natural cresylic acid feedstocks by this process. Cresylic acid products containing more than 0.1% total neutral oil are not acceptable under current standards. A cresylic acid product containing about 1% neutral oil, such as can be obtained (at the very best) from a typical tar oil distillate feedstock with aqueous methanol/hexane, would have to be causticized on an industrial scale, and steamed to further remove neutral oil to meet today's product specification. The discovery of the present invention provides a high purity cresylic acid product for which causticizing and steaming, with all of the associated drawbacks and costs, can be eliminated.

Due to the relatively high viscosity of the mixed solvent heavy phase, the preferred embodiment of the invention utilizes a multistage mixer/settler, with feedstock pumped to an intermediate stage, to achieve countercurrent fractional liquid/liquid extraction, although other types of extraction equipment could be used. In the mixer/settler embodiment, pumps and static mixers can be used at each stage to obtain thorough mixing of the two phases and a true equilibrium stage, which is difficult to obtain with other countercurrent extractor designs with this viscous a heavy solvent. A ten stage mixer/settler is preferred, although more or less stages could be employed. Preheating of the feed materials to 135° F. or more and maintenance of the chosen temperature in the mixer/settler lowers the viscosity of the heavy phase and this enhances the ability of the two phases to disengage between mixing stages. Temperatures exceeding the atmospheric boiling point of the light solvent could be employed to good benefit, provided the extraction equipment is operated at pressures above atmospheric pressure.

The preferred composition of the heavy solvent is in the range of 65% to 85% glycerol, the balance being triethylene glycol. When the feed is tar oil distillate, 65% to 75% is preferred, and for a crude phenols material (depitched and dried extract from gas liquor), 85% is preferred. However, the invention would still be useful at other solvent compositions. Other polyhydric alcohols could be employed, such as diethylene glycol, but the preferred cosolvent to be used with glycerol is triethylene glycol, since cresylic acid is separable from triethylene glycol without having to use too many theoretical plates in the distillation to recover cresylic acid from the heavy solvent pair. The preferred light solvent is hexane, although other paraffinic, or cycloparaffinic solvents could be used such as heptane, octane, cyclohexane, petroleum ether, etc. Aromatic solvents could also be employed, or mixtures of these materials.

The ratio of heavy solvent to feed is in the range of about 2:1 to 4:1, and the ratio of light solvent to feed is in the range of about 2:1 to 8:1. These ratios will vary depending on the particular feed and desired degree of purification. The preferred ratio of heavy solvent to tar oil distillate feed is 4:1 and the preferred ratio of light solvent to this feed is also 4:1. This ratio provides high purity and good recovery, although ratios below and above these are also useful.

Referring to the drawing, the process of the present invention begins by pumping the feedstock, either sprung dry raw phenolics from desulfurized refinery spent caustic, or a coal tar oil distillate rich in cresylic acid, or a dried and depitched crude phenols extract from gas liquor, or any of the above in a dephenolized state, through line 2, to a feed preheater 4 to warm the stream to 135° F. or more. Although this heating is optional, it is preferred. The heated feedstock is then fed to the feed stage of a mixer/settler 6 or other countercurrent side feed liquid/liquid extractor, preferably of about ten equilibrium stages more or less. Simultaneously the heavy solvent is pumped through line 8 and through heavy solvent preheater 10 to warm the stream to 135° F. or more, and then the heated heavy solvent is fed to the mixing chamber of stage ten of the mixer/settler. At the same time, the light non-polar solvent is pumped through line 12, through light solvent preheater 14 to heat it to 135° F. or more, and then to the mixing chamber of stage one of the mixer/settler. Each stage of the mixer/settler is equipped with a solvent mixing chamber, the contents of which are pumped (optionally through a static mixing element), to a settling chamber. The overflow of this settling chamber is the light solvent which is decanted to the next stage in the direction of flow of the light solvent. The underflow of this settling chamber is directed to a heavy phase collection chamber and decanted from there to the next stage in the direction of flow of the heavy solvent. The heavy solvent is removed from stage one of the mixer/settler at line 16, and pumped through a feed preheater 18 to distillation column 20, wherein the cresylic acid is removed from a condenser 22 as a distillate product through line 24, ready to be fed to a tar base removal step, and then for sale or fractionation into distillate products. From the reboiler 26 of this column is removed through line 28 the heavy solvent, which is pumped to a flash distillation column 30 or a falling film evaporator, for the purpose of flashing the heavy solvent to separate it from polymeric materials, removed through line 32, which are in the heavy solvent as a consequence of having been heated in the reboiler 26 of column 20. The polymeric materials should be removed, since they tend to cause emulsion problems in the mixer/settler. The depitched heavy solvent is pumped through line 8, to be used again in the mixer/settler. The hexane or other light solvent is removed from stage ten of the mixer/settler through line 34, and pumped through feed preheater 36 to a distillation column 38, from which the light solvent distillate is removed through line 12 from a condenser 40, and from there the light solvent is recycled through feed preheater 14 as described above, to the mixer/settler. The distillation column 38 produces neutral oil as a bottoms product through line 42 (the neutral oil can be used as a feedstock for naphthalenes, or it can be combusted for fuel value). Depending on the temperatures chosen for the liquids fed to the mixer/settler, it may or may not require to be operated under pressure.

EXAMPLE #1

A feedstock consisting of tar oil distillate having a boiling range including the cresylic acid fraction, from phenol through the $C_9$ phenols, was prepared by distilling coal tar oil derived from gasification of lignite. This feedstock was found to have a composition as shown in Table 1.

TABLE 1

| Substance | weight percent (or ppm) |
| --- | --- |
| phenol | 5.4% |
| total cresols | 12.0% |
| total ethylphenols | 4.6% |
| total xylenols | 8.4% |
| guaiacol | 0.8% |
| 4-methylguaiacol | 0.7% |
| methylguaiacol | 0.1% |
| total $C_9$ phenols (trace of $C_{10}$) | 6.4% |
| total phenols | 38.4% |
| total neutral oil (by difference) | 57.9% |
| benzonitrile | 3335 ppm |
| total tar bases | 3.35% |

This feedstock was pumped to stage six of a pilot plant scale ten stage mixer/settler at the rate of 3.4 kg. per hour. It was preheated to a temperature of 135° F. Prior to introducing feedstock, hexane, at a rate of 13.8 kg./hour, and heavy solvent (65% by weight glycerol, and 35% by weight triethylene glycol), at a rate of 14.0 kg./hour, were pumped into the mixer/settler at stages one and ten, respectively, in order to establish their liquid levels and flows. These two solvents were preheated to a temperature of 135° F. The mixer/settler was insulated, so as to minimize heat loss. The weight ratio of heavy solvent to feed was 4.1:1, and of the light solvent to feed was 4.1:1.

From a light solvent draw-off located at the tenth stage, a solution of neutral oil in hexane was drawn off at the rate of 16.1 kg./hour, and this material was pumped to a flow buffering tank, and from there to stage 31 of a 78 theoretical stage distillation column (a number of stages much in excess of what was needed, but expedient for our purposes), 6" in diameter, from which hexane was recovered as an overhead product for recycle, at the rate of 13.8 kg/hour, and from which neutral oil was recovered as a bottoms product, at a rate of 2.3 kg./hour. This column was operated at atmospheric pressure, and a reflux ratio of 1.5.

From a heavy solvent draw-off located at the first stage, a solution of cresylic acid dissolved in the heavy solvent was drawn off at the rate of 15.1 kg./hour, and this material was pumped to a flow buffering tank and from there to stage 11 of a 22 theoretical stage distillation column, 6" in diameter, from which cresylic acid was recovered as an overhead product at a rate of 1.1 kg./hour, and from which the heavy solvent mixture was recovered as a bottoms product at a rate of 14.0 kg./hour. This column was operated at a pressure of 21 mm Hg in the reboiler (10 mm Hg at the top of the tower), and at a reflux ratio of 8.

The heavy solvent bottoms product was pumped to a flow buffering tank, and from there to a flash drum at the rate of 14.0 kg./hour. The flash drum was operated at a pressure of 10 mm Hg. The reboiler was occasionally drawn down, to remove accumulated pitch-like substances. The overhead, produced at the rate of very nearly 14.0 kg./hour, was pumped to a flow buffering tank, and from there it was continually reintroduced to the mixer/settler.

The amount of cresylic acid removed from the system in the heavy solvent was determined, and the amount contained in the hexane phase from the mixer/settler was determined, and based on material balance calculations and analytical data, the cresylic acid recovery was found to be 92.1% of that found in the feed to the system.

The cresylic acid overhead product from the heavy solvent recovery column was treated with sulfuric acid to remove tar bases and achieve a further reduction in cyclopentenones, and then analyzed, and found to have a composition as shown in Table 2.

TABLE 2

| Substance | weight percent (or ppm) |
| --- | --- |
| phenol | 14.0% |
| total cresols | 35.1% |
| total ethylphenols | 13.6% |
| total xylenols | 22.4% |
| guaiacol | 2.0% |
| 4-methylguaiacol | 1.2% |
| methylguaiacol | 0.2% |
| total C$_9$ phenols (trace C$_{10}$) | 11.4% |
| total phenols | 99.9% |
| total neutral oil | less than 800 ppm |
| including | |
| cyclopentenones | 210 ppm* |
| benzonitrile | 142 ppm |
| methylbenzonitriles | 40 ppm |
| steam volatile neutral oil | 380 ppm |

TABLE 2-continued

| Substance | weight percent (or ppm) |
| --- | --- |
| including | |
| naphthalene | 8 ppm |
| acetophenone | 62 ppm |
| 1-methylnaphthalene | 9 ppm |
| 2-methylnaphthalene | 5 ppm |

*lower limit of detection/reliable quantitation is 150 ppm

The data from this pilot plant run show that the present invention is capable of providing a 92% recovery of cresylic acid having less than 800 ppm total impurities following the removal of tar bases from the product of the process.

EXAMPLE #2

The feedstock consisted of a mixture of coal-derived cresylic acid materials, primarily an extract from gas liquor, and encompassed in boiling range ortho-cresol through the C$_9$ phenols (the phenol fraction was removed, and additionally, the guaiacols were removed). This feedstock was analyzed, and found to have a composition as shown in Table 3.

TABLE 3

| Substance | weight percent (or ppm) |
| --- | --- |
| phenol | 0.3% |
| total cresols | 77.9% |
| total ethylphenols | 7.8% |
| total xylenols | 10.8% |
| total C$_9$ phenols (including 0.26% C$_{10}$) | 1.8% |
| total phenols | 98.6% |
| total neutral oil | 1.37% |
| including | |
| benzonitrile | 2200 ppm |
| steam volatile neutral oil | 1.15% |
| including | |
| naphthalene | 2283 ppm |
| acetophenone | 602 ppm |
| 1-methylnaphthalene | 1209 ppm |
| 2-methylnaphthalene | 2318 ppm |
| total tar bases | nil |

This feedstock was pumped to stage six of a pilot plant scale ten stage mixer/settler at the rate of 3.7 kg. per hour. It was preheated to a temperature of 135° F. Prior to introducing feedstock, hexane, at a rate of 21.8 kg./hour, and heavy solvent (85% by weight glycerol, and 15% by weight triethylene glycol), at a rate of 14.7 kg./hour, were pumped into the mixer/settler at stages one and ten, respectively, in order to establish liquid levels and flows of these. These two solvents were preheated to a temperature of 135° F. The mixer/settler was insulated, so as to minimize heat loss. The ratio of heavy solvent to feed was 4.0:1, and the ratio of hexane to feed was 5.9:1.

From a light solvent draw-off located at the tenth stage, a solution of neutral oil in hexane was drawn off at the rate of 22.0 kg./hour, and this material was pumped to a flow buffering tank, and from there to stage 31 of a 78 theoretical stage distillation column, 6" in diameter, from which hexane was recovered as an overhead product for recycle, at the rate of 21.8 kg./hour, and from which neutral oil was recovered as a bottoms product, at the rate of 0.2 kg./hour. This column was operated at atmospheric pressure, and a reflux ratio of 2.

From a heavy solvent draw-off located at the first stage, a solution of cresylic acid dissolved in the heavy solvent was drawn off at the rate of 18.2 kg./hour, and this material was pumped to a flow buffering tank, and from there to stage 11 of a 22 theoretical stage distillation column, 6" in diameter, from which cresylic acid was recovered as an overhead product at the rate of 3.5 kg./hour, and from which the heavy solvent mixture was recovered as a bottoms product, at the rate of 14.7 kg./hour. This column was operated at a pressure of 18 mm Hg in the reboiler (10 mm Hg at the top of the tower), and a reflux ratio of 4.4.

The heavy solvent bottoms product was pumped to a flow buffering tank, and from there to a flash drum at the rate of 14.7 kg./hour. The flash drum was operated at a pressure of 10 mm Hg. The reboiler was occasionally drawn down, to remove accumulated pitch-like substances. The overhead, collected at the rate of very nearly 14.7 kg./hour, was continually reintroduced to the mixer/settler.

The amount of cresylic acid removed from the system in the heavy solvent was determined, and the amount contained in the hexane phase from the mixer/settler was determined, and based on material balance calculations and analytical data, the cresylic acid recovery was found to be 96.8% of that found in the feed to the system.

The cresylic acid overhead product from the heavy solvent recovery column was analyzed, and found to have a composition as shown in Table 4.

TABLE 4

| Substance | weight percent (or ppm) |
|---|---|
| phenol | 0.3% |
| total cresols | 79.0% |
| total ethylphenols | 7.9% |
| total xylenols | 11.0% |
| total $C_9$ phenols (including trace $C_{10}$) | 1.8% |
| total phenols | 99.98% |
| total neutral oil including | less than 200 ppm |
| cyclopentenones | not detectable* |
| benzonitrile | 128 ppm |
| methylbenzonitriles | less than 40 ppm |
| steam volatile neutral oil including | 35 ppm |
| naphthalene | 1 ppm |
| acetophenone | 6 ppm |
| 1-methylnaphthalene | less than 1 ppm |
| 2-methylnaphthalene | less than 1 ppm |

*lower limit of detection/reliable quantitation is 150 ppm

The data from this pilot plant run show that with a low neutral oil feedstock, such as obtained by way of extraction of gas liquor, the present invention is capable of providing a 96.8% recovery of cresylic acid containing less than 200 ppm total impurities.

We claim:

1. A process for producing a purified natural cresylic acid product derived from a natural cresylic acid feedstock including in its boiling range phenol through $C_9$ phenols and containing impurities consisting of neutral oil substances, said process comprising the steps of:

a. distilling said natural cresylic acid feedstock to produce a mixture which includes in its boiling range said phenol through the $C_9$ phenols and said impurities;

b. feeding said mixture to an intermediate mixture feed stage of a countercurrent liquid/liquid fractional extractor having a plurality of stages including a heavy solvent feed stage at one end thereof, a light solvent feed stage at the other end thereof and an intermediate mixture feed stage;

c. feeding to said heavy solvent feed stage a heavy solvent consisting of 65 to 85% glycerol and 35 to 15% of another polyhydric alcohol solvent having a boiling range such that said heavy solvent will be separable by distillation from said natural cresylic acid product and thereby forming a heavy solvent phase containing said purified natural cresylic acid;

d. feeding to said light solvent feed stage a light solvent selected from the group consisting of a paraffinic substance, a cycloparaffinic substance, an aromatic substance and mixtures thereof, having a boiling range such that said light solvent will be separable by distillation from said impurities and thereby forming a light solvent phase containing said impurities;

e. removing at said one end of said extractor said heavy solvent phase containing said purified natural cresylic acid and vacuum distilling said heavy solvent phase to separate said purified natural cresylic acid product from said heavy solvent;

f. removing said light solvent phase at said other end of the extractor and distilling to separate said light solvent from said, impurities; and g. recycling said separated light solvent to step d and said separated heavy solvent to step c.

2. A process as recited in claim 1 wherein the step g of recycling said heavy solvent further includes the step of distilling at least a portion of said separated heavy solvent from step e to remove high boiling pitch impurities prior to said recycle to step c.

3. A process as recited in claim 1 wherein said feedstock is distilled to remove the phenol prior to step a.

4. A process as recited in claim 1 wherein said feedstock further contains cresols and wherein said feedstock is distilled to remove the phenol and at least some of the cresols prior to step a.

5. A process as recited in claim 1 wherein said polyhydric alcohol solvent is triethylene glycol.

* * * * *